United States Patent [19]

Drake et al.

[11] 4,407,786

[45] Oct. 4, 1983

[54] GLASS COMPOSITION

[75] Inventors: Cyril F. Drake, Harlow; Mary Tripp, Bishop's Stortford, both of England

[73] Assignee: International Standard Electric Corporation, New York, N.Y.

[21] Appl. No.: 252,662

[22] Filed: Apr. 9, 1981

Related U.S. Application Data

[62] Division of Ser. No. 97,019, Nov. 23, 1979.

[30] Foreign Application Priority Data

Dec. 21, 1978 [GB] United Kingdom ............... 49600/78

[51] Int. Cl.³ .......................... C03C 3/16; A61K 33/34
[52] U.S. Cl. ....................................... 424/14; 424/127;
424/131; 424/132; 424/133; 424/140; 424/148;
424/150; 424/144; 426/2; 604/93; 604/57;
501/33; 501/35; 501/45; 501/47; 501/48;
501/73; 501/24
[58] Field of Search ........................ 501/45, 48, 33, 35, 501/24; 424/14, 140

[56] References Cited

U.S. PATENT DOCUMENTS

| | | | |
|---|---|---|---|
| 1,654,404 | 12/1927 | Blumenberg | 501/24 X |
| 2,532,386 | 12/1950 | Armistead | 501/74 |
| 3,338,670 | 8/1967 | Fuchs | 501/48 |
| 3,640,827 | 2/1972 | Lutz | 501/48 X |
| 3,746,556 | 7/1973 | Morgan | 501/48 X |
| 3,762,909 | 10/1973 | Davie et al. | 501/47 X |
| 3,807,981 | 4/1974 | Contrea et al. | 501/45 |
| 3,923,527 | 12/1975 | Matsuura | 501/48 X |
| 3,958,973 | 5/1976 | Roberts | 501/45 X |
| 4,042,402 | 8/1977 | Drake et al. | 501/77 |
| 4,098,610 | 7/1978 | Wexell | 501/77 |
| 4,123,248 | 10/1978 | Drake | 501/45 X |
| 4,283,227 | 8/1981 | Drake | 501/47 |

Primary Examiner—Helen M. McCarthy
Attorney, Agent, or Firm—John T. O'Halloran; David M. Quinlan

[57] ABSTRACT

A copper phosphate water soluble glass composition. The composition of the glass may be adjusted so as to release copper at a uniform preselected rate and to produce a desired pH in the resultant solution. In one application of the glass copper may be supplied to an animal from an implant formed from a cupric oxide/phosphorus pentoxide glass which also incorporates one or more glass modifying oxides such as alkali metal oxides and alumina, to control the glass solubility. Suitable glasses comprise 5-55 mole % cupric oxide + alkali metal oxides. 45-75 mole % phosphorus pentoxide, and not more than 15 mole % alumina, where the copper oxide concentration is not less than 5 mole %.

3 Claims, 6 Drawing Figures

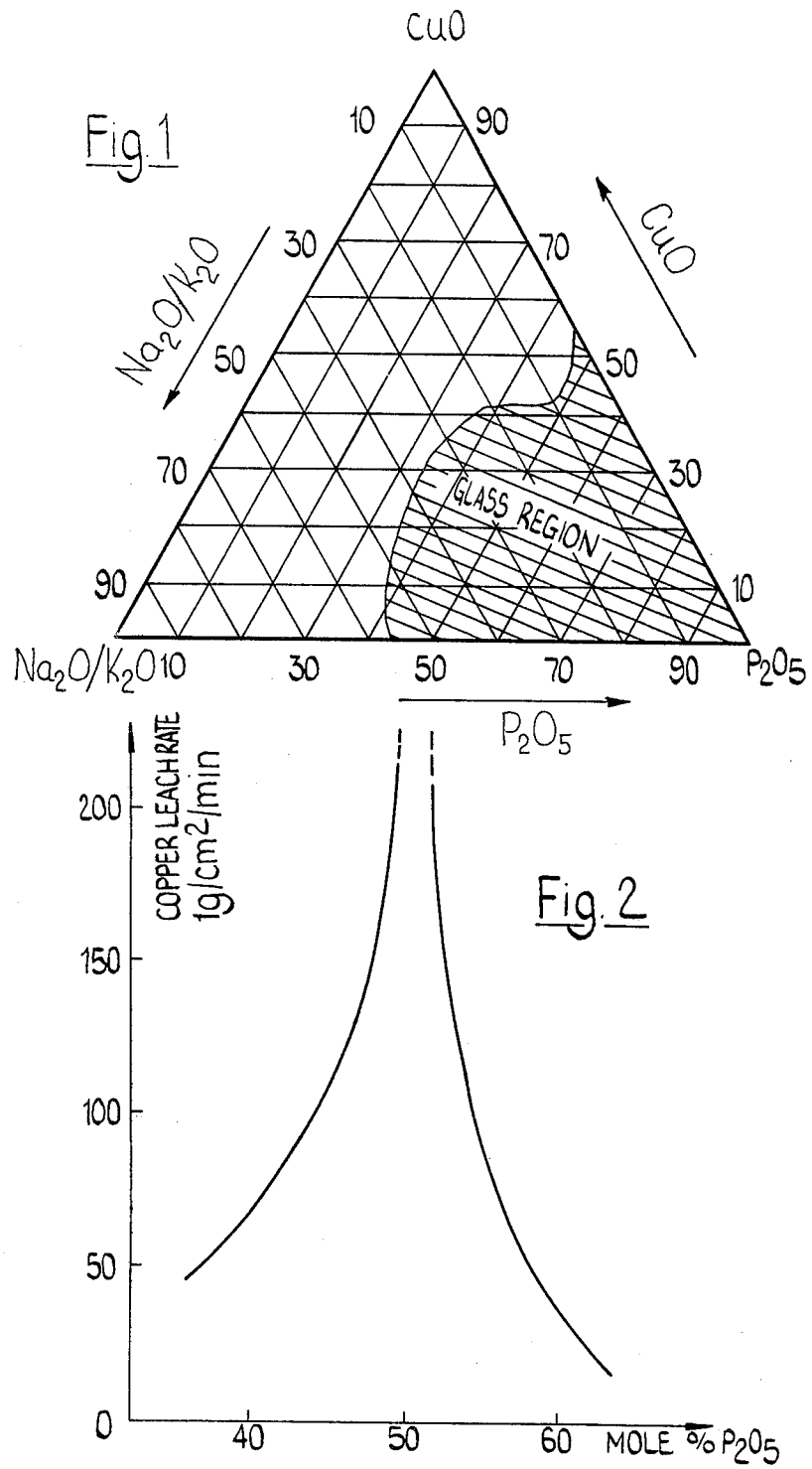

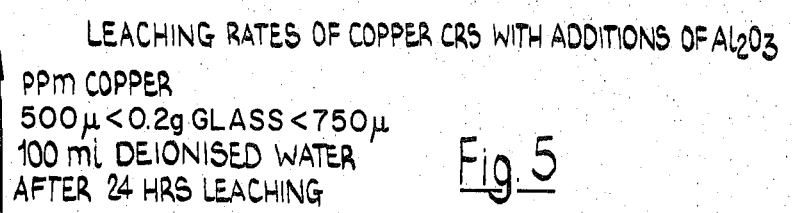
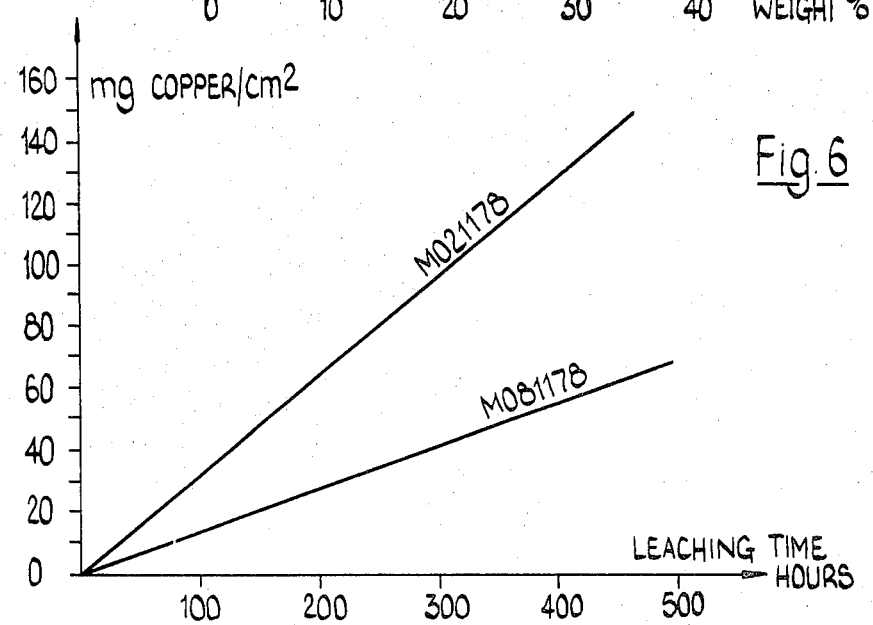

GLASS COMPOSITION

This is a division of application Ser. No. 97,019, filed Nov. 23, 1979.

This invention relates to glass compositions, and in particular to water soluble glasses which release cations at a controlled rate to an aqueous environment.

There are situations where it is desirable to release copper ions into an aqueous environment at a controlled rate. In some cases the required rate of release may be such that the totality of the copper added to the system is released in a short period of hours or days and in other applications it may be required that the total added is slowly released at a substantially uniform rate over a period extending for months or even years. In particular cases there may be additional requirements. For example, it may be essential that no residue remains after the material end as the source of copper ions is exhausted. In other cases, where copper is made available as supplement to improve the health of an animal, it will be essential that my materials other than copper which are simultaneously released should be physiologically harmless. In yet other cases, it may be necessary to ensure that the pH of the resulted solution does not fall outside defined limits.

This invention relates to vitreous copper-containing materials which can be designed to meet the requirements outlined above.

One of the problems involved in the husbandry of domesticated animals, e.g. cattle and sheep, is the provision of an adequate supply of trace elements in the animals diet. In regions where such trace elements are naturally deficient it is customary to supplement such materials either in the form of a medication which is periodically administered, or in the form of an additive to the animals foodstuff. In practice however, because the required quantities of trace elements are so small it is difficult to achieve the required dosage rate. Furthermore, at levels above the required dosage rate, certain trace elements are dangerous poisons.

U.S. Pat. No. 4,283,227, assigned to the assignee of this application describes a subcutaneous implant for an animal and adapted to supply one or more trace elements, such as selenium into the bloodstream or body fluid of the animal, the implant comprising a body of a glass material at least the major portion of which includes selenium dioxide together with zinc oxide.

According to one aspect of the invention there is provided a glass composition, comprising a total of 5 to 55 mole % of cupric oxide and sodium and/or potassium oxide, 45 to 75 mole % phosphorus pentoxide, and not more than 15 mole % alumina, and wherein the cupric oxide content of the glass is not less than 5 mole %.

According to another aspect of the present invention there is provided a subcutaneous implant for supplying one or more trace elements to the bloodstream or body fluid of an animal, the implant comprising a partially or wholly water soluble glass body formed from a glass forming oxide together with one or more glass modifying oxides, said body incorporating the one or more trace elements in oxide form.

According to a further aspect of the invention there is provided a subcutaneous implant for supplying copper to the bloodstream or body fluid of an animal, the implant comprising cuprous and/or cupric oxide incorporated in a wholly or partially water soluble glass body formed from a glass forming oxide together with one or more glass modifying oxides.

The term glass modifying oxide is understood to mean an oxide which, whilst it does not of itself form a glass, is capable of forming glass compositions in conjunction with one or more other, glass forming oxides. Typical oxides which fall into this category are the oxides of the metals of Groups IA and IIA IIIB and IVB of the Periodic Table, and also many transition metal oxides. In the composition described herein the glass modifying oxide or oxides is/are chosen so as to provide the finished glass composition with suitable solubility characteristics.

Embodiments of the invention will now be described with reference to the accompanying drawings in which:

FIG. 1 is a phase diagram of the cupric oxide/phosphorus pentoxide/alkali metal oxide glass system;

FIG. 2 illustrates the relationship between phosphorus pentoxide concentration and water solubility of the glasses of FIG. 1;

FIG. 5 shows the effect of alumina addition to the glasses; and

FIG. 6 shows the dissolution characteristics of two typical glass compositions.

Figure 3:
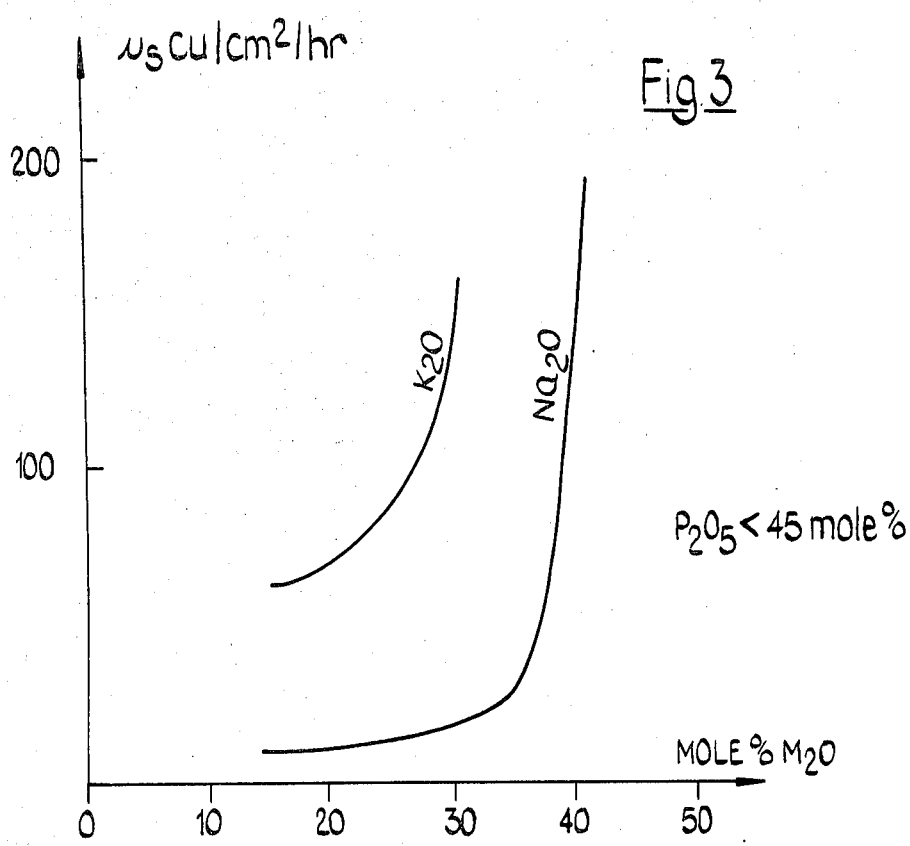
FIG. 3 illustrates the relationship between alkali metal content and water solubility of the glasses of FIG. 1.

Referring to FIG. 1, the glass compositions described herein lie within the glass-forming region, shown shaded, of the cupric oxide/phosphorus pentoxide/alkali metal oxide phase diagram. The alkali metal is typically sodium, potassium or mixtures thereof. Also the glass composition may include minor proportions of other glass-modifying metal oxides e.g. $Al_2O_3$. Similarly, a small proportion of the phosphorus pentoxide may be replaced by other glass-forming oxides such as silica or boric oxide. The addition of minor proportions of such oxides to control the properties of the glass will be familiar to those skilled in the art.

It should be understood that, although the various constituents of the glass are referred to as oxides they may of course exist in the form of other compounds, e.g. phosphates. For ease of calculation however, each constituent is expressed as its oxide.

To prepare the glasses the various components of the glass system in the form of oxides, or compounds which on heating decompose to form oxides, are fused to form an homogeneous melt which is then cooled to room temperature to form a glass, or is processed directly into the required form for example, glass spheres or rods. A portion of such a rod or one or more glass spheres may then be inserted beneath the skin of an animal where the constituents of the glass slowly dissolve into the bloodstream or body fluid of the animal.

In particular, glass compositions suitable for supplying controlled quantities of copper to an animal may be prepared by co-melting measured quantities of phosphorus pentoxide, which provides the glass forming oxide of the system, glassmodifying oxides such as alumina and an alkali metal or alkaline-earth metal oxide and cupric oxide. The materials are fused at a temperature in the range 900° to 1300° C. and in an oxidising atmosphere for a sufficient period of time to form an homogeneous melt. The melt may then be cast and cooled, or, advantageously, one or more glass rods may be drawn from the melt.

Where a rod of the glass material has been formed, this may be subdivided into short lengths which may then be implanted, e.g. with the aid of a suitable hypodermic needle, beneath the skin of an animal so as to release copper into the animal's bloodstream or body fluid.

The rate at which copper is released from the glass is determined both by the copper content of the glass and its solubility. The latter is determined by the composition of the glass and is a function of a number of factors. Thus, referring to FIG. 2, it can be seen that the phosphorus pentoxide content of such a glass has a marked effect on its solubility. The solubility curve, which is typical for a glass composition within the shaded area of the phase diagram of FIG. 1, has a maximum value for a phosphorus pentoxide content of about 50 mole %. The exact value of this maximum has not been determined as such glasses have an extremely high solubility. It should be noted that the solubility curve of FIG. 2 is exhibited by those glasses in which the alkali metal content is below 30% where the alkali metal is sodium, or below 15 mole % where the alkali metal is potassium.

FIG. 3 shows the effect of alkali metal content on the water solubility of the glasses. As can be seen the alkali metal has little effect below a particular value, 15 mole % for potassium and 30 mole % for sodium, but above that value further addition of alkali metal oxides cause a large increase in water solubility. The solubility curves shown in FIG. 3 relates to glass in which the phosphorus pentoxide content is below 45 mole %.

Figure 4:
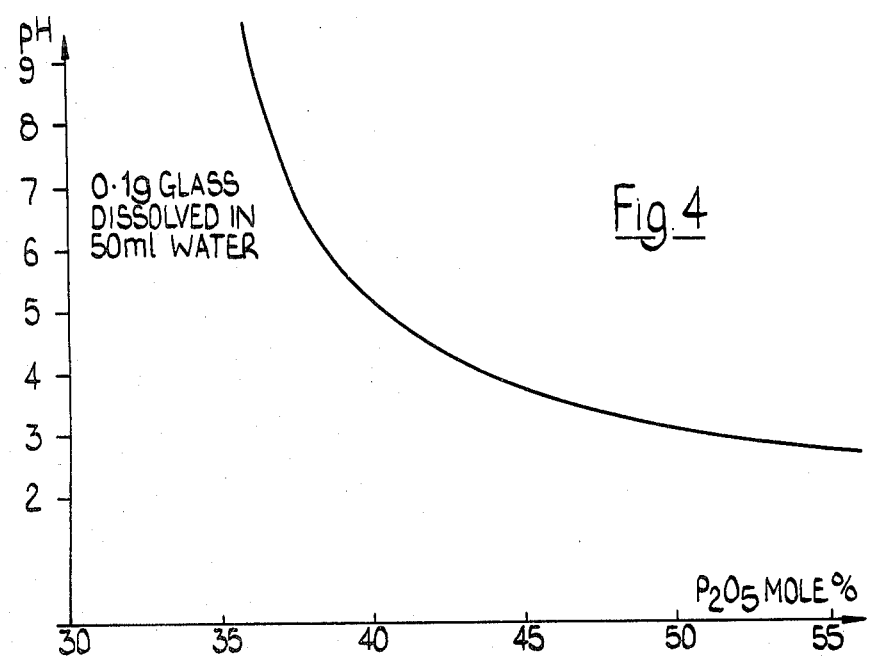
FIG. 4 illustrates the relationship between phosphorus pentoxide concentration and solution pH of the glasses of FIG. 1.

In physiological applications the pH of an aqueous solution formed from the glass may be of some importance. It has been found that the solution pH may be determined by the phosphorus pentoxide content of the glass, this effect being illustrated in FIG. 4. The pH relationship was determined by dissolving 0.1 g samples of a series of glasses in 50 mls deionised water. As can be seen from FIG. 4 any pH value between 2.8 and 9.0 can be obtained by switchable choice of phosphorus pentoxide content.

In certain applications the glass compositions containing only cupric oxide, phosphorus pentoxide and a alkali metal may be somewhat too soluble when selected to provide a desired pH value. To reduce the solubility one or more glass modifying oxides may be included in the composition. In particular aluminium oxide ($Al_2O_3$) may be employed for this purpose. The effect of alumina addition to such glasses is shown in FIG. 5, and it can be seen that relatively small concentrations of alumina produce a marked reduction in water solubility.

For many purposes the maximum alumina content will not exceed 4 mole %, although for certain applications, e.g. where the glass is in the form of a fine powder and a low solubility is therefore required, the alumina content may be increased to as much as 15 mole %.

The glass compositions described herein may be employed for supplying copper into aqueous solution in a variety of environments. Thus the glasses may be used as ferilizers for supplying small quantities of copper to copper deficient soils, in the preparation of salt licks for domesticated animals, or a fungicides, moluscicides or algicides. Advantageously the glasses may be employed in the form of implants, which may comprise rods, spheres or pellets of the glass, which may be inserted beneath the skin of an animal by means of a hypodermic needle. Copper is then slowly released in therapentic quantities into the bloodstream of the animal. Such an implant may also include minor quantities of other trace elements such as boron, arsenic, iodine, manganese, chromium, silver, gold and gallium.

Preferred glass composition for releasing copper into aqueous solution comprises a total of 5 to 55 mole percent of cupric oxide together with an alkali metal oxide, and from 75 to 45 mole percent phosphorus pentoxide. To provide an adequate release of copper, the cupric oxide content of the glass shall not be less than 5 mole percent.

The following examples illustrate the invention:

EXAMPLE I

To illustrate the effect of glass composition on the solution rate of a glass and also to demonstrate the fact that the glasses continue to dissolve at a uniform rate for long periods of time, in fact until they have completely passed into solution, two glasses were prepared having the composition:

| Batch No. | CuO mole percent | $P_2O_5$ mole % |
|---|---|---|
| MO81178 | 43.8 | 56.2 |
| Mo21178 | 51.3 | 48.7 |

The glasses were prepared by fusion of cupric oxide and phosphorus pentoxide in air followed by casting on to a cold steel plate and crunching. Weighed samples of the glasses were immersed in water and their weight loss determined over a period of time, the results being illustrated in the graph shown in FIG. 6 of the accompanying drawings.

EXAMPLE II

This example illustrates the technique of solubility control wherein predetermined quantities of a glass modifying oxide, in this case alumina, are added to the glass.

A base glass was prepared having the composition 51.3 mole % cupric oxide and 48.7 mole % phosphorus pentoxide. This base glass was divided into several portions each of which was fused with a differed weighed quantity of alumina to provide a homogeneous glass composition. The phases were cast and crushed to a particle size between 500 and 750 microns, and 0.2 g sample of each glass composition were immersed in 100 ml of deionised water at a temperature of 20° C. The copper content of the water was determined in each case after 24 hour, the results being summarised in the graph shown in FIG. 5 of the accompanying drawings. As can be seen, relatively low concentrations of alumina cause a dramatic reduction of solubility, and at alumina concentrations above 4 mole % the glass is small. It should be noted that in some applications, for example those in which the glass is used in the form of very fine particles (e.g. $<2\mu$) it may be necessary to have a very low solution rate (in terms of amount of glass dissolved per unit area in unit time) because of the very large surface area consequent or the small particle size. In such a case, amounts of $Al_2O_3$ in excess of 4% may be necessary to reduce even further the solution rate and it was found that the amount may be increased up to the glass-forming limit of 15 mole %.

We claim:

1. A subcutaneous implant for supplying copper to the bloodstream or body fluid of an animal, the implant comprising a glass body completely soluble in the body fluid of the animal for releasing copper into solution at a predetermined uniform rate when implanted beneath the skin of the animal and leaving no residue when completely dissolved, wherein the glass body consists of cupric oxide as the source of copper, at least one alkali metal oxide as a first glass-modifying oxide, 45 to 75 mole percent phosphorous pentoxide as a glass-forming oxide present in the glass body in a predetermined concentration chosen to provide a solution with the body fluids of the animal having a pH physiologically compatible with the animal, and sufficient alumina as a second glass-modifying oxide to reduce the solubility of the glass body to the predetermined uniform rate suitable for supplementing the copper ingested by the animal from other sources to provide the total amount of copper necessary for nutrition without toxic side effects, and wherein the cupric oxide concentration is not less than 5 mole percent, said cupric oxide and alkali metal oxide concentration together is 5 to 55 mole percent, wherein the alkali metal oxide is an oxide of sodium or potassium or a combination thereof, and the alumina concentration is not more than 4 mole percent.

2. The implant recited in claim 1 wherein the glass body is at least one spherical, rod-shaped or pellet-shaped form suitable for subcutaneous injection into the animal with a hypodermic needle.

3. A method of supplying copper to the bloodstream of an animal with a subcutaneous implant that releases copper as it dissolves in the body fluids of the animal and leaves no residue when completely dissolved, the method comprising:

providing the glass body recited in claim 1 or 2, wherein the composition of the glass body provides a solution with the body fluids of the animal having a pH physiologically compatible with the animal and releases copper at a uniform rate that supplements the copper ingested by the animal from other sources to provide the total amount of copper necessary for proper nutrition without toxic side effects; and implanting said glass body beneath the skin of the animal.

* * * * *